United States Patent [19]

Huang et al.

[11] Patent Number: 4,895,867
[45] Date of Patent: Jan. 23, 1990

[54] 2-(5-PHENYL-2-FURANYL)IMIDAZOLES USEFUL AS CARDIOTONIC AGENTS

[75] Inventors: Chau-Ting Huang; Stanford S. Pelosi, Jr.; Ralph L. White, Jr., all of Norwich, N.Y.

[73] Assignee: Norwich Eaton Pharmaceuticals, Inc., Norwich, N.Y.

[21] Appl. No.: 145,073

[22] Filed: Jan. 19, 1988

Related U.S. Application Data

[63] Continuation-in-part of Ser. No. 878,910, Jun. 26, 1986, abandoned.

[51] Int. Cl.$^4$ .................. C07D 405/54; A61K 31/415
[52] U.S. Cl. ..................................... 514/397; 548/336
[58] Field of Search ........................ 548/336; 514/397

[56] References Cited

U.S. PATENT DOCUMENTS

| | | | |
|---|---|---|---|
| 3,927,023 | 12/1975 | Brown et al. | 260/309.6 |
| 3,985,891 | 10/1976 | Kutter et al. | 514/300 |
| 3,993,643 | 11/1976 | Henry et al. | 260/240 A |
| 4,012,414 | 3/1977 | Pelosi, Jr. | 548/336 |
| 4,012,415 | 3/1977 | Pelosi, Jr. et al. | 548/336 |
| 4,012,416 | 3/1977 | Pelosi, Jr. et al. | 548/336 |
| 4,021,444 | 5/1977 | Pelosi, Jr. | 260/309.6 |
| 4,022,798 | 5/1977 | Pelosi, Jr. | 260/309.6 |
| 4,144,347 | 3/1979 | Stern | 548/336 |
| 4,297,360 | 10/1981 | Lesher et al. | 546/257 |
| 4,405,635 | 9/1983 | Schnettler et al. | 548/321 |
| 4,411,908 | 10/1983 | Chapleo et al. | 548/348 |
| 4,559,354 | 12/1985 | Fuhrer et al. | 514/357 |

FOREIGN PATENT DOCUMENTS

1436089  5/1976  United Kingdom ............... 514/357

*Primary Examiner*—Mary C. Lee
*Assistant Examiner*—Zinna Northington Davis
*Attorney, Agent, or Firm*—David L. Suter; Stephen T. McMahon; Milton B. Graff, IV

[57] ABSTRACT

The present invention involves certain 2-(5-phenyl-2-furanyl)-imidazoles, pharmaceutical compositions containing such compounds, and methods for enhancing the contractile force of cardiac muscle of a mammal which comprises systemically administering such compounds to a mammal.

7 Claims, No Drawings

2-(5-PHENYL-2-FURANYL)IMIDAZOLES USEFUL AS CARDIOTONIC AGENTS

CROSS REFERENCE TO RELATED APPLICATION

This application is a continuation-in-part of prior application Ser. No. 878,910, now abandoned filed June 26, 1986.

TECHNICAL FIELD

The present invention relates to compounds and compositions which are useful as cardiotonic agents, and to the treatment of a mammal to increase the contractility of its heart.

BACKGROUND OF THE INVENTION

Heart failure is an abnormality in cardiac function that results from the inability of the heart to pump blood commensurate with the body's needs. Failure develops from a depression in myocardial contractility which can occur due to ischemic heart disease, hypertension, non-obstrusive cardiomyopathies and certain types of congenital heart disease.

As used herein, a cardiotonic agent is a substance which enhances the cardiac output, i.e. quantity of blood pumped by the heart of a mammal to which it is administered. It is advantageous to achieve such increased cardiac output with little or no increase in the rate of heartbeat of the mammal. This is accomplished by achieving a greater quantity of blood pumped by each beat of the heart.

Certain 2-(5-phenyl-2-furanyl)imidazoles are known, and it has been disclosed that some of these compounds have antidepressant, antihypertensive, or skeletal muscle relaxant activity. The following references disclose certain 2-(5-phenyl-2-furanyl)imidazoles and methods of synthesizing them and are hereby incorporated by reference: U.S. Pat. No. 4,012,414 issued to Pelosi on Mar. 15, 1977; U.S. Pat. No. 4,012,415 issued to Pelosi & Yu on Mar. 15, 1977; and U.S. Pat. No. 4,012,416 issued to Pelosi on Mar. 15, 1977.

South African patent application No. 813070 filed by Ciba-Geigy AG in the names of Fuhrer, Ostermayer, & Zimmermann, published May 26, 1982, discloses a group of 2-(3-carbamoyl-4-hydroxyphenoxy)ethylamino compounds that act in a specific manner on betaadrenergic receptors and exhibit cardiotonic activity. Among the many constituents disclosed in the reference that can be attached to this active center is an ((imidazol-2-yl)-2-furyl) phenoxy group. In Example II of the disclosure where synthesis of such a compound is described, several 2-(5-phenyl-2-furanyl)imidazoles are disclosed as intermediate compounds in the synthesis of the compounds of interest.

References which disclose compounds having structures similar to the (2-(5-phenyl-2-furanyl)imidazoles of the present invention include the following U.S. Pat. Nos. 3,927,023 issued to Brown & Shavel on Dec. 16, 1975; 3,993,643 issued to Henry & Cory on Nov. 23, 1976; 4,021,444 issued to Pelosi on May 3, 1977; 4,022,798 issued to Pelosi on May 10, 1977; 4,144,347 issued to Stern on Mar. 13, 1979; 4,289,526 issued to Worthington, de Fraine, Rathmel & Gatehouse on Sept. 15, 1981; and 4,411,908 issued to Chepleo & Myers on Oct. 25, 1983.

References which disclose certain cardiotonic agents include the following U.S. Pat. Nos. 3,985,891 issued to Kutter, Austel & Diederen on Oct. 12, 1976; 4,004,012 issued to Lesher & Opalka on Jan. 18, 1977; 4,032,575 issued to Ikezaki, Ito, Okazaki, Hoshiyama, Nagao & Nakajima on June 28, 1977; 4,289,772 issued to Campbell, Danilewicz, Evans & Ham on Sept. 15, 1981; 4,297,360 issued to Lesher, Opalka & Page on Oct. 27, 1981; 4,397,854 issued to Sircar on Aug. 9, 1983; and 4,405,635 issued to Schnettler, Dage & Crisar on Sept. 20, 1983.

SUMMARY OF THE INVENTION

It is an object of the present invention to provide a method of enhancing the cardiac output of a mammal.

It is a further object of this invention to provide such enhanced cardiac output of a mammal with little or no increase in the rate of heartbeat of the mammal.

It is also an object of this invention to provide novel compounds which enhance the cardiac output of a mammal.

It is also an object of this invention to provide pharmaceutical compositions which enhance the cardiac output of a mammal.

The present invention provides a method for enhancing the contractile force of cardiac muscle of a mammal which comprises systemically administering to such mammal an effective amount of a composition comprising a compound conforming to the following chemical structure:

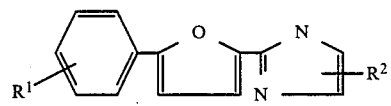

wherein R' is mono- or di- substituents selected from the group consisting of hydrogen, halo, nitro, trifluoromethyl, straight and branched chain $C_1$–$C_5$ alkyl, acetyl, propionyl, methoxy and ethoxy; and $R^2$ is mono- or di- substituents selected from the group consisting of hydrogen, methyl, and ethyl; and pharmaceutically acceptable salts and/or hydrates thereof.

DETAILED DESCRIPTION OF THE INVENTION

In one of its aspects, the present invention is a method for enhancing the cardiac output of a mammal which comprises systemically administering to a mammal having a depressed level of cardiac output an effective amount of a composition comprising certain 2-(5-phenyl-2-furanyl)imidazoles as cardiotonic agents. The 2-(5-phenyl-2-furanyl)imidazoles found to be useful as cardiotonic agents conform to the chemical structure:

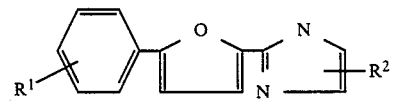

wherein $R^1$ is mono- or di- substituents selected from the group consisting of hydrogen, halo, nitro, trifluoromethyl, straight and branched chain $C_1$–$C_5$ alkyl, acetyl, propionyl, methoxy and ethoxy; and $R^2$ is mono- or di- substituents selected from the group consisting of hydrogen, methyl, and ethyl; and pharmaceutically acceptable salts and/or hydrates thereof (Compounds A).

Preferred 2-(5-phenyl-2-furanyl)imidazoles useful in the present invention include compounds which conform to the chemical structure of Compounds A but wherein $R^2$ is hydrogen; other preferred 2-(5-phenyl-2-furanyl)imidazoles include compounds which conform to the chemical structure of Compounds A but wherein $R^2$ is mono- or di-substituents selected from the group consisting of methyl and ethyl.

More preferred compounds are Compounds A wherein $R^1$ comprises a constituent selected from the group consisting of halo and trifluoromethyl; other more preferred compounds are Compounds A wherein $R^1$ is selected from the group consisting of hydrogen, 2-fluoro, 2-chloro, 4-chloro, 2-bromo, 4-bromo, 4-iodo, 3-trifluoromethyl, 4-trifluoromethyl, 4-methyl, 4-isopropyl, 4- methoxy, 2,4-dichloro, 3,4-dichloro, 2,4- dibromo, 2-bromo-4-methyl, 2-methyl-4-bromo, 3-trifluoromethyl-4-bromo, 3-methoxy-4-bromo, and 2-nitro-4-methoxy.

The cardiotonic activity of compounds of the present invention can be demonstrated using the primary screening test method set forth in the following reference: Evans, D. B., R. E. Weishaar & H. R. Kaplan, "Strategy for the Discovery and Development of a Positive Inotropic Agent", *Pharmacology and Therapeutics*, Vol. 16 (1982), pp. 303–330. This test measures the effects of such compounds on the contractility of cardiac tissue excised from the atrial muscle of a guinea pig.

An additional or alternative method for testing the cardiotonic activity of compounds of the present invention is set forth in the following reference: Beek, O. G., "A Small Animal Model for Monitoring Inotropic Responses to Cardiotonic Agents", *Journal of Pharmacological Methods*, Vol. 7 (1982), pp. 321–329. Right ventricular inotropic responses are measured in an anesthetized, close-chested guinea pig using a pressure-sensitive transducer inserted into the right ventricle of the heart via the right jugular vein.

Compounds of the present invention have demonstrated enhanced cardiac output in mammals to which they have been administered according to one or both of the above screening tests. In addition, compounds of the present invention generally provide such enhanced cardiac output to mammals with little or no effect on heartbeat rate or rhythm.

TEST METHODS

Test Method I

In vitro guinea pig atrial muscle contractile force measurement

Unfasted male Hartley albino guinea pigs, weighing 450–650 g (Charles River Breeding Laboratories, Inc., Wilmington, MA) were used in these studies. They were killed by cranial concussion at the beginning of the experiment. The heart was quickly removed into a Petri dish filled with a solution of the following composition (in water): NaCl 99.0 mM; Dextrose 11.0 mM; 4.7 mM; $MgSO_4$ 1.2 mM; $NaH_2PO_4$ 1.3 mM; $CaCl_2.2H_2O$ 2.5 mM; $NaHCO_3$ 25.01 mM; bubbled with 95% $O_2$:5% $CO_2$ at room temperature. A triple O silk ligature was tied to the edge of the left atrial appendage, using an intestinal needle. The appendage was cut off; a section was cut away from the wall which faced the heart, retaining a sheet of tissue from the outer face of the atrium. The tissue was mounted from a pair of point stimulating electrode hooks with 1 gram of tension in an organ bath maintained at 30° C. The ligature was tied to a Grass FT-103 force-displacement transducer, and responses were measured in grams of developed tension with a Grass Model 7 polygraph (Grass Instrument Co., Quincy, MA). The left atria were stimulated electrically with the following square wave parameters: 3 v; 4 msec 1 Hz, as soon as they were put into the baths. After a short time (3–5 minutes), voltage was increased until stable responses were obtained (10–25% above threshold). The tissues were allowed to equilibrate under such stimulation for at least 1 hour before experimentation.

The test compounds were dissolved in water, if water soluble, or if not, in tetrahydrofurfuryl alcohol (Eastman D5C) or in an organic vehicle containing 90% polyethylene glycol, 6% ethanol, 3% propylene glycol and 1% $H_2O$). (Test compound solution concentrations were selected to keep injection volumes between 1 and 10 μl).

Isoproterenol (0.54 to 5.4 nM) was given at the beginning of each experiment to confirm the viability and responsiveness of the tissues. Test agents were given in several graded doses in logarithmic increments. Responsiveness to isoproterenol was also assessed at the end of the experiment unless other positive drug responses were obtained near the end of the experiment.

Results were expressed as percent change from control for contractile force. The $EC_{50}$ value (calculated concentration required to increase the contractile force by 50% from the control level) for each tissue was obtained, where possible, by regression analysis. The mean of the $EC_{50}$ values was obtained from at least three individual tissues for each compound tested.

TEST METHOD II

In vivo guinea pig ventricular pressure measurement

Unfasted male Hartley albino guinea pigs, weighing 450–650 g (Charles River Breeding Laboratories, Inc., Wilmington, MA) were used in these studies. Under ethyl carbamate (urethane) anesthesia (1.25 g/kg i.p.), the trachea was cannulated through a mid-ventral cervical incision. The left carotid artery was cannulated with PE-50 tubing (Clay Adams Co., Parsippany, NJ) filled with 100 g/ml heparin for blood pressure monitoring, and the left jugular vein was cannulated (catheter filled with saline) for drug administration. A 3Fr Millar Mikro-Tip ventricular pressure catheter (Millar instruments, Inc., Houston, Texas) was positioned in the right ventricle via the right jugular vein. A thoracotomy was performed and the guinea pig was respired by a rodent respirator (Model 680, Harvard Apparatus Co., Millis, MA) at a rate of 8 ml/stroke×40 strokes/minute. A modified Brodie strain gauge (Warren Research Products, Charleston, South Carolina) was sutured on the right ventricle parallel to, but avoiding, the intraventricular septum. The rectal body temperature of 37° C. was maintained by an electronic temperature controlled lamp. The animals were left undisturbed for 60 minutes before being used for an experiment.

A single i.v. bolus does of 0.3 μg/kg isoproterenol was administered followed by a 0.2 ml saline flush prior to and at the end of each experiment to check the viability and responsiveness of each animal. Usually a vehicle does in a volume equal to the single largest volume of compound to be administered was intravenously injected 20–30 minutes after the initial isoproterenol injection when parameters had returned to baseline levels. A non-cumulative dose response curve was determined for each compound using a minimum of 3 doses. Time between doses for all compounds was dependent upon the time needed for all parameters to return to baseline or stable levels. A minimum of 3 animals per dose level was tested for each compound.

Results were expressed as percent changes from pre-treatment baseline for all parameters measured. The $ED_{50}$ values of ventricular pressure changes (calculated dose required to increase the right ventricular pressure by 50% from the control level) of test compounds were determined by regression analysis.

EXAMPLES 1-34

Compounds having the following chemical structure were tested for cardiotonic activity according to one or both of the above test methods:

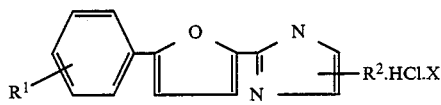

Determinations of contractile force $EC_{50}$ according to Test Method I and ventricular pressure $ED_{50}$ according to Test Method II which have been obtained for the compounds are provided in Table I:

ences incorporated by reference hereinabove: Pelosi '414, Pelosi & Yu '415, and Pelosi '416.

Novel compounds of the present invention include compounds of the class of 2-(5-phenyl-2-furanyl)imidazoles which conform to the chemical structure of Compounds A except where $R^1$ is hydrogen or 2-nitro or 4-nitro or 4-acetyl or 3-trifluoromethyl or 3,4-dimethoxy, and $R^2$ is hydrogen (Compounds B).

Preferred novel compounds of the present invention include Compounds B but wherein $R^2$ is hydrogen. Other preferred 2-(5-phenyl-2-furanyl)imidazoles include compounds which conform to the chemical structure of Compounds A but wherein $R^2$ is mono- or di-substituents selected from the group consisting of methyl and ethyl. More preferred 2-(5-phenyl-2-furanyl)imidazoles include compounds which conform to the chemical structure of Compounds A but wherein $R^2$ is 1-methyl, 1-ethyl, 4-ethyl, or especially 4-methyl.

More preferred novel compounds of the present invention include Compounds B where $R^1$ comprises a substituent selected from the group consisting of halo and trifluoromethyl. Other still more preferred novel compounds are Compounds A wherein $R^1$ comprises 2-halo or 4-halo, especially when such halo is chloro or bromo. Particularly preferred are such compounds wherein $R^1$ comprises 2-halo or 4-halo and wherein a further $R^1$ substituent is nil or consists of a substituent in

TABLE 1

| Example | $R^1$ | $R^2$ | X | Contractile Force $EC_{50}$ ($\mu M$) | Ventricular Pressure $ED_{50}$ (mg/kg) |
|---|---|---|---|---|---|
| 1 | 4-nitro | hydrogen | ¼ $H_2O$ | 260 | — |
| 2 | 4-chloro | hydrogen | — | 3.5 | 0.31 |
| 3 | 3-trifluoromethyl | hydrogen | — | 6.5 | — |
| 4 | 3,4-dimethoxy | hydrogen | — | 190 | 3.16 |
| 5 | 2-nitro | hydrogen | — | 60 | 29.15 |
| 6 | hydrogen | hydrogen | — | 22.9 | 1.98 |
| 7 | 4-acetyl | hydrogen | — | 40 | — |
| 8 | 2-bromo | hydrogen | ¼ $H_2O$ | 5.7 | 0.80 |
| 9 | 2-chloro | hydrogen | — | 3.7 | — |
| 10 | 2-fluoro | hydrogen | — | 7.2 | — |
| 11 | 2-trifluoromethyl | hydrogen | — | 28.2 | — |
| 12 | 2,4-dichloro | hydrogen | — | 1.3 | 2.05 |
| 13 | 3,4-dichloro | hydrogen | — | 5.4 | — |
| 14 | 4-bromo | hydrogen | — | 1.3 | — |
| 15 | 4-fluoro | hydrogen | — | 33.4 | — |
| 16 | 4-trifluoromethyl | hydrogen | — | 3.0 | — |
| 17 | 2-nitro-4-methoxy | hydrogen | — | 8.2 | — |
| 18 | 2-bromo | 1-methyl | — | 21.1 | — |
| 19 | 4-methyl | hydrogen | — | 3.7 | — |
| 20 | 4-isopropyl | hydrogen | — | 6.8 | — |
| 21 | 2,4-dibromo | hydrogen | ¾ $H_2O$ | 8.0 | — |
| 22 | 4-bromo | 1-methyl | — | >100* | — |
| 23 | 4-bromo | 4-methyl | — | 0.5 | — |
| 24 | 2,6-dibromo | hydrogen | — | >100* | — |
| 25 | 2-bromo-4-methyl | hydrogen | — | 1.5 | — |
| 26 | 3-trifluoromethyl-4-bromo | hydrogen | — | 4.0 | — |
| 27 | 4-iodo | hydrogen | — | 10.3 | — |
| 28 | 4-methoxy | hydrogen | — | 28.0 | — |
| 29 | 3-methoxy-4-bromo | hydrogen | — | 3.4 | — |
| 30 | 2-bromo | 1-ethyl | — | 21.2 | — |
| 31 | 2-methyl-4-bromo | hydrogen | — | 1.9 | — |
| 32 | 2-bromo | 4-methyl | — | 1.7 | — |
| 33 | 4-bromo | 1,5-dimethyl | — | 50.2 | — |
| 34 | 4-bromo | 1,4-dimethyl | ¼ $H_2O$ | >100* | — |

*Active, but insufficient data to determine $EC_{50}$

Another aspect of the present invention is certain 2-(5-phenyl-2-furanyl)imidazoles which are novel compounds and are useful as cardiotonic agents.

Novel compounds of the present invention include compounds of the class of 2-(5-phenyl-2-furanyl)imidazoles which conform to the chemical structure of Compounds A except for such 2-(5-phenyl-2-furanyl)imidazoles which are disclosed in the following referthe 3- position or especially in the alternate (4- or 2-) position; such further substituent is preferably halo, especially chloro or bromo; $C_1$-$C_3$ alkyl, especially methyl; trifluoromethyl; or methoxy. Other more preferred novel compounds are Compounds A wherein $R^1$ comprises 2- or 4- $C_1$-$C_3$ alkyl (most preferred is methyl), especially 4- $C_1$-$C_3$ alkyl. Other still more preferred compounds are Compounds B wherein $R^1$ is selected from the group consisting of 2-fluoro, 2-chloro, 4-chloro, 2-bromo, 4-bromo, 4- iodo, 4-methyl, 4-isopropyl, 4-methoxy, 2,4-dichloro, 3,4-dichloro, 2,4-dibromo, 2-bromo-4-methyl, 2-methyl-4-bromo, 3-trifluoromethyl-4-bromo, 3-methoxy-4-bromo, 2-nitro4-methoxy, or 4-trifluoromethyl.

Compounds of the present invention can be synthesized using the following general stepwise procedure or a modification thereof which is within the purview of a skilled organic chemist:

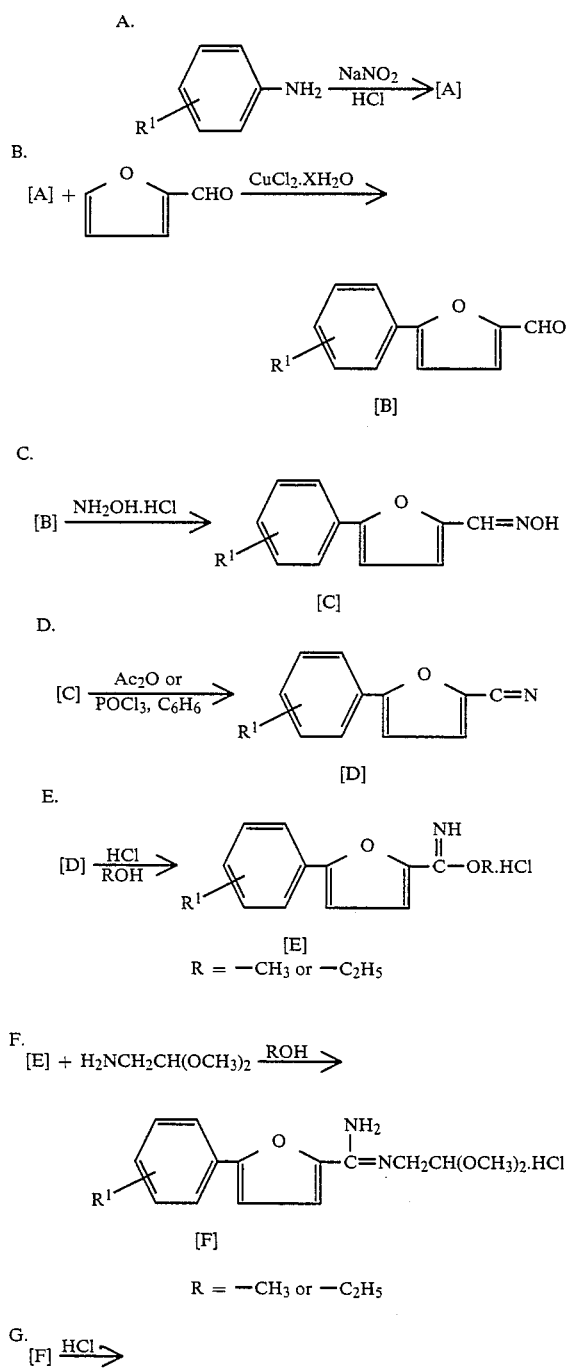

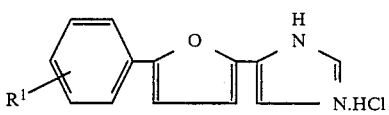

The following non-limiting examples provide methods for synthesizing the novel compounds of the present invention:

EXAMPLE 35

2-[5-(4-Methylphenyl-2-furanyl]-1H-imidazole Hydrochloride (Compound of Example 19)

A. & B. A mixture of p-toluidine (216 g, 2.0 moles) (Aldrich Chemical Co., Milwaukee, Wisconsin) in water (400 ml) and concentrated HCl (540 ml) was diazotized by dropwise addition of solution of $NaNo_2$ (144 g, 2.08 moles) (Aldrich Chemical Co.) in water (400 ml) with the pot temperature kept below 10° C. The mixture was stirred for ½ hr and furfural (246 g, 2.56 moles) (Aldrich Chemical Co.) was added, followed by a solution of $CuCl_2. \times H_2O$ (46 g) in water (300 ml). The stirred mixture was heated at 40–50° C. For 5 hours and stored overnight at room temperature. The product was extracted with ether (1200 ml), dried overnight over $MgSO_4$ and Darco (activated carbon—Aldrich Chemical Co.), filtered and the filtrate stripped of solvent under reduced pressure. The residue was distilled in vacuo, collecting the product, 5-(p-methylphenyl)-2-furaldehyde (B) at 160–180° C./1.4 mm Hg; yield: 70 g (19%).

C. A solution of hydroxylamine hydrochloride (26 g, 0.38 mole) (Aldrich Chemical Co.) in water (65 ml) was added to a solution of B (70 g, 0.38 mole) in absolute ethanol (200 ml), then stirred for 20 minutes and cooled overnight. The product, 5-(p-methylphenyl-2-furaldehyde oxime (C), was collected by filtration; yield: 60 g (79%).

D. A mixture of 44 g (0.22 mole) of C in 450 ml of acetic anhydride was heated at reflux for 3½ hours with near dissolution. The reaction mixture was cooled and added to ice. The resulting solid, 5-(4-methylphenyl)-2-furancarbonitrile (D), was filtered, washed with water and air dried to yield 39 g (100%).

E. A solution of 18 g (-.10 mole) of D in 350 ml of absolute ethanol was cooled in an ice bath and saturated with HCl gas. The resulting solution was stirred in the cold for 30 minutes and then at room temperature for 1½ hours. Using vacuum distillation ca. 300 ml of solvent was removed. The resulting solid was filtered, washed with cold ethanol, and dried in a vacuum desiccator to yield 22 g (93%) of ethyl 5-(4-methylphenyl)-2-furan-carboximidate hydrochloride (E).

F. A solution of 16 g (0.060 mole) of E in 200 ml of absolute ethanol was treated with 7.4 g (0.070 mole) of aminoacetaldehyde dimethyl acetal (Aldrich Chemical Co.) all at once. The resulting solution was heated at reflux for 6½ hours. The reaction mixture was cooled and the resulting solid was filtered, washed with cold ethanol and air dried to yield 9.1 g (b 47%) of N-(2,2-dimethoxyethyl)-5-(4-methyl)-2-furancarboximidamide hydrochloride (F).

G. A mixture of 9.1 g (0.028 mole) of F in 125 ml of 3N HCl was heated at 70–75° C. for 6½ hours and then allowed to stand at room temperature for 72 hours. The solid was filtered, washed with cold water, recrystallized from isopropanol and dried in a vacuum desiccator to yield 4.0 g (55%) of 2-[5-(4-methylphenyl)-2-furanyl]-1H-imidazole hydrochloride; m.p. 285-295° C.

Anal. calc'd for $C_{14}H_{12}N_2O \cdot HCl$: C, 64.50; H, 5.03; N, 10.74. Found: C, 64.50: H, 4,97; N, 10.68.

EXAMPLE 36

2-[5-[4-(1-Methylethyl)phenyl]-2-furanyl]-1H-imidazole Hydrochloride (Compound of Example 20)

A. & B. A mixture of 100 g (0.74 mole) of 4-isopropylaniline (Aldrich Chemical Co.), 100 ml of water, and 200 ml of concentrated hydrochloric acid, was cooled at 5° C. and treated dropwise with a solution of 52 g (0.75 mole) of sodium nitrite in 150 ml of water. The mixture was kept at 5° C. for 1 hour. A solution of 90 g (0.94 mole) of furfural in 150 ml of acetonitrile was added all at once followed by a solution of 30 g of $CuCl_2 \cdot XH_2O$ in 125 ml of water. The reaction mixture was stirred overnight at ambient temperature. The reaction mixture was warmed at 45° C. for 30 minutes and then cooled, and extracted with ether (3×400 ml). The combined ethereal extracts were washed with water (3×200 ml), saturated $NaHCO_3$ solution (2×200 ml) and water (2×200 ml). The ethereal extract was dried over $MgSO_4$ and the solvent removed in vacuo (water pump). The residual oil was distilled under high vacuum using a flame. The product, 5-[4-(1-methylethyl)phenyl]-2-furancarboxaldehyde (B), was obtained as an oil (26 g, 16% yield); b.p. 160–175° C./0.5 mm Hg.

C. A solution of 26 g (0.12 mole) of B in 125 ml of ethanol was treated with a solution of 8.4 g (0.12 mole) of hydroxylamine hydrochloride in 10 ml of water. The mixture was stirred for 5 hours at ambient temperature. The resulting solid was filtered, washed with ethanol and air dried to yield 15 g (55%) of 5-[4-(1-methylethyl)-phenyl]-2-furancarboxaldehyde oxime (C).

D. A mixture of 15 g (0.066 mole) of C and 150 ml of acetic anhydride was heated to reflux with dissolution. The solution was heated at reflux for 3½ hours, and then cooled and added to ice. The resulting solid was filtered, washed with water and dried in a vacuum desiccator to yield 13.5 g (100%) of 5-[4-(1-methylethyl)-phenyl]-2-furancarbonitrile (D).

E. A near solution of 13.5 g (0.0640 mole) of D in 300 ml of absolute ethanol was cooled in an ice bath and saturated with dry HCl gas. The resulting solution was stirred in the cold for 30 minutes and then at room temperature for 1 hour. The volume of the solution was reduced by two-thirds in vacuo. The resulting solid was filtered, washed with cold ethanol, and dried in a vacuum desiccator to yield 14.3 g (74%) of 5-[4-(1-methylethyl)phenyl]-2-furancarboximidate hydrochloride (E).

F. A mixture of 14.3 g (0.0490 mole) of E in 200 ml of absolute ethanol was treated with 6.3 g (0.060 mole) of aminoacetaldehyde dimethyl acetal. The reaction mixture was heated to reflux with dissolution. The reaction mixture was heated at reflux for 6½ hours. Upon cooling, no solid formed. The solvent was removed in vacuo yielding a semi-solid. This material was triturated several times with ether. The still sticky semi-solid was stirred in 100 ml of ethyl acetate at reflux. The mixture was cooled and the resulting solid filtered, and air dried to yield 14 g (81%) of N-(2,2-dimethoxy-ethyl)-5-[4-(4-methylethyl)phenyl]-2-furancarboximidamide hydrochloride (F).

G. A mixture of 8.0 g (0.023 mole) of F and 125 ml of 3N HCl was heated at 70-75° C. for 6½ hours and then allowed to stand for 72 hours at room temperature. The solid was filtered, washed with cold water, and partially air dried. The solid was heated in isopropanol with Darco and filtered hot. The filtrate was cooled in an ice bath and the product was precipitated by the addition of ether. The solid was filtered, washed with ether and dried in a vacuum desiccator to yield 5.75 g (87%) of 2-[5-[4-(4-methylethyl)phenyl]-2-furanyl]-1H-imidazole hydrochloride; m.p. 206°–208° C.

Anal. calc'd for $C_{16}H_{16}N_2O \cdot HCl$: C, 66.55; H, 5.93; N, 9.70. Found: C, 66.33; H, 6.32; N, 9.39.

EXAMPLE 37

2-[5-(4-Bromo-3-methoxyphenyl)-2-furanyl]-1H-imidazole Hydrochloride (Compound of Example 29)

O. 2-Bromo-5-nitroanisole (25 g, 0.116 mole) (Fairfield Chemical Co., Blythewood, South Carolina) was dissolved in 150 ml of 70:30 methanol/ethyl acetate. Raney nickel (1.0 g) was added to the solution. The mixture was hydrogenated on a Parr shake for 3 hours, then filtered through celite. The dark brown filtrate was treated with Darco and concentrated under reduced pressure to a brown solid. The solid was dissolved in 50:50 ethyl acetate/hexane (1 L) and filtered through a 2-inch cake of silica gel (column grade). The resulting solution was concentrated under reduced pressure to a solid yielding 19.3 g (89%) of 4-bromo-3-anisidine (O). The NMR was consistent with the structure of O.

A. & B. 4-Bromo-3-anisidine (17.5 g, 0.093 mole) was stirred in distilled water (150 ml) containing concentrated HCl (30 ml) and cooled to 0° C. in an ice water bath. A solution of sodium nitrite (6.4 g, 0.093 mole) in water (30 ml) was added and the mixture was stirred at 0° C. After 1 hour, furfural (11.17 g, 0.116 mole) and cupric chloride dihydrate (5.11 g, 0.004 mole) were added. The mixture was allowed to warm to room temperature and stir for 72 hours. The reaction was then filtered yielding 22.43 g (86%) of a dark brown solid product, 5-(4-bromo-3-methoxyphenyl)-2-furancarboxaldehyde (B). The IR was consistent with the structure of B (aldehyde carbonyl at 1660 cm$^{-1}$). C. & D. B (19.6 g, 0.070 mole), anhydrous sodium acetate (11.48 g, 0.14 mole) and hydroxylamine hydrochloride (9.73 g, 0.14 mole) were combined and refluxed in SDA-32 (400 ml) (U.S. Industrial Chemical Co., Westport, Connecticut) containing water (31 ml) for 5 hours. Heat was removed and the mixture was allowed to cool to room temperature and stir for 20 hours. The reaction was then poured into ice water and upon warming to room temperature, a solid formed. The solid oxime was collected by filtration and allowed to air dry for 20 hours.

The above oxime was refluxed in acetic anhydride (400 ml) for 2.5 hours. The solution was poured into crushed ice and allowed to stand for 20 hours. The solid that formed was collected by filtration and air dried. The solid was then dissolved in 1.5 L of 1:3 ethyl acetate/hexane and stirred for 0.5 hour with 200 g of silica gel. The mixture was filtered and the filtrate was concentrated under reduced pressure to an orange solid yielding 9.82 g (57%) of product, 5-(4-bromo-3-methoxyphenyl)-2-furancarbonitrile (D). The IR was consistent with the structure of D (nitrile at 2245 cm$^{-1}$).

E. D (4.28 g, 0.017 mole) was stirred in methanol (60 ml). Sodium methoxide (0.75 g) (Aldrich Chemical Co.) was added and the mixture was heated at 45° C. using an oil bath. Upon heating, a solution formed and it was stirred at 45° C. for 20 hours. The reaction was then poured into ice water to precipitate a solid. The solid was collected by filtration and allowed to air dry. The solid was dissolved in methanol (50 ml) and methanolic HCl was added in small amounts until the solution was acidic. The solution was cooled in an ice bath and ether was added until the solution turned cloudy. A precipitate formed and was collected by filtration and rinsed with ether yielding 4.5 g (75%) of 5-(4-bromo-3-methoxyphenyl-2-furancarboximidate hydrochloride (E).

F. & G. E (4.35 g, 0.013 mole) and aminoacetaldehyde dimethyl acetal (1.7 ml, 0.016 mole) were combined and refluxed in ethanol (65 ml) for 4 hours. The solution was cooled to room temperature and the solvent was removed on a rotary evaporator. The brown residue was stirred at 68° C. in 3N HCl for 20 hours.

The reaction was allowed to cool to room temperature and was then filtered. The solid was rinsed with cold water and allowed to air dry yielding 4.31 g (97%) of 2-[5-(4-bromo-3-methoxyphenyl)-2-furanyl]-1H-imidazole hydrochloride (G). An analytical sample was prepared by recrystallization from methanol/ether yielding 0.56 g (56%) of G. The NMR and IR were consistent with the structure of G. The melting point was 301–302° C.

Anal. calc'd for $C_{14}H_{11}BrN_2O_2 \cdot HCl$: C, 47.28; H, 3.40; N, 7.88. Found: C, 46.99; H, 3.49; N, 7.58.

EXAMPLE 38

2-[5-(4-Bromo-2-methylphenyl)-2-furanyl]-1H-imidazole Hydrochloride (Compound of Example 31)

A. & B. To a mixture of 4-bromo-2-methylaniline (100 g, 0.5375 mole) (Aldrich Chemical Co.) in water (270 ml) and concentrated HCl (190 ml) under stirring at 0° C. was added dropwise a solution of sodium nitrite (37.25 g, 0.5399 mole in 200 ml water). The reaction temperature was kept below 5° C. during this addition. The semisolution was allowed to stir at 0–5° C. for 2 hours. Furfural (45 ml, 0.53 mole) was added, followed by a solution of cupric chloride dihydrate (12.146 g, 0.071 mole in 82 ml water) and the mixture was allowed to warm up to room temperature. The reaction mixture was stirred 21 hours. A brown solid was filtered off and triturated in SDA-30 (U.S. Industrial Chemical Co.) to give 13.53 g (9.5% yield) of first crop. After letting the reaction filtrate sit for 4 days, a second crop was filtered off and triturated in SDA-30 to give 31.0 g of 5-(4-bromo-2-methylphenyl)-2-furancarboxaldehyde (B). Total yield was 43.53 g (31%).

C. & D. B (13.53 g, 0.0510 mole) was combined with hydroxylamine hydrochloride (7.482 g, 0.1077 mole), soldium acetate (14.07 g, 0.1034 mole), SDA-32 (425 ml) and water (35 ml). The mixture was refluxed for 4½ hours and then allowed to cool to room temperature. Pouring the mixture into ice water precipitated a solid. After 24 hours of standing, the mixture was filtered and the pale yellow solid air dried to give 13.77 g (96% yield) of oxime.

The oxime (39.67 g, 0.1416 mole) was refluxed in acetic anhydride (610 ml, 6.47 mole) for 3 hours and cooled to room temperature. Pouring the solution into ice water and stirring the resulting mixture for 2 hours before filtering gave a tan/brown solid which was washed well with water and air dried. Triturating this solid in hexane gave a resulting solid which was impure by TLC. The solid was dissolved in hot cyclohexane and silica gel (Kieselge 60-Krackeler Scientific Inc., Albany, New York) added. After stirring the mixture 15 minutes, it was filtered and the filtrate was concentrated to a solid, 5-(4-bromo-2-methylphenyl)-2-furancarbonitrile (D), (11.15 g, 56% yield).

E. To a solution of D (11.15 g, 0.0425 mole) in 300 ml of anhydrous methanol was added sodium methoxide (0.209 g, 0.0039 m) and the solution was allowed to stir at room temperature overnight. The solution was poured onto crushed ice and white solid separated which was collected, dissolved in ether, dried over anhydrous magnesium sulfate and then filtered. To the filtrate was added saturated methanolic HCl until acidic and the resulting solid was collected to give 12.71 g (90% yield) of 5-(4-bromo-2-methylphenyl)-2-furancarboximidate hydrochloride (E).

F. & G. A solution of E (12.71 g, 0.0384 mole), absolute alcohol (145 ml) and aminoacetaldehyde dimethyl acetal (5.2 ml, 5.02 g, 0.0477 mole) was refluxed for 3 hours. The solution was then concentrated to a white solid which was combined with 3N HCl (120 ml) and the resulting mixture was heated at 65°–73° C. for 4 hours. The mixture was stirred overnight. Collecting and air drying the solid gave 12.66 g (97% yield) which was recrystallized from n-propanol (70 ml) to give 3.95 g (31% yield) of 2-[5-(4-bromo-2-methylphenyl)-2-furanyl]-1H-imidazole hydrochloride (G); m.p. 247°–251° C.

Anal. calc'd for $C_{14}H_{12}BrClN_2O$: C, 49.51; H, 3.56: N, 8.25. Found: C, 49.37; H, 3.92; N, 8.26.

EXAMPLE 39

2-[5-(2-Bromophenyl)-2-furanyl]imidazole Hydrochloride Tetartohydrate (Compound of Example 8)

A. & B. To a pasty mixture of 172 g (1.0 mole) of 2-bromoaniline (Aldrich Chemical Co.) in 500 ml of water and 350 ml of concentrated HCl under stirring at 0° C. was added dropwise a solution of sodium nitrite (70 g, 1.0 mole) in 400 ml of water. The addition was completed in about 1¼ hours while keeping the reaction temperature at 3°–8° C. After the solution was completed, the solution was allowed to stir at 0°–5° C. for ½ hour. Then 96 g (1.0 mole) of furfural and 23 g of cupric chloride dihydrate in 150 ml of water were added and the mixture was allowed to warm up gradually with stirring. Bubbling was noticeable at 10°–15° C. while brown solid formed gradually. After stirring overnight at ambient temperature, the reaction mixture was filtered and the gummy brown solid was washed well with water and air-dried. The filtrate was allowed to stand further for a week since bubbling was still evident. More gummy brown solid was obtained. The solid was triturated with 2-propanol to give 110 g (44% yield) of a grayish solid, 5-(2-bromophenyl)-2-furancarboxaldehyde (B).

C. & D. A mixture of 75 g (0.3 mole) of B, 42 g (0.6 mole) of hydroxylamine hydrochloride, 50 g (0.6 mole) of anhydrous sodium acetate in 2.5L of SDA-32 and 200 ml of water was heated at reflux for 5 hours. After cooling, the reaction mixture was poured onto crushed ice. Yellow solid separated gradually and was collected, washed well with water and air-dried. The yield of oxime was 61 g.

The above oxime was placed in 750 ml of acetic anhydride and heated at reflux for 3 hours. After cooling, mixture was poured onto crushed ice and allowed to stand overnight. The mixture was filtered and the gummy brown solid was washed well with water and air-dried. The solid was then boiled with hexane and the top hexane solution was decanted from the gummy material at the bottom. On cooling, orange yellow solid separated from the hexane solution. The solid, 5-(2-bromophenyl)-2-furancarbonitirile (D), was collected, washed with hexane and air-dried. The yield was 35 g (47%).

E. A mixture of D (25.9 g, 0.145 mole) and anhydrous methanol was heated to 45° C. Sodium methoxide (0.5 g) was introduced, and stirring was continued for 4 hours. The solution was poured into ice water (ca. 1.5L) yielding a solid which was filtered, washed with water and air dried. This material (36 g) was introduced in small increments into HCl saturated anhydrous ether (ca. 300 ml). The solid, methyl 5-(2-bromophenyl)-2-furancarboximidate hydrochloride (E), was filtered and washed with anhydrous ether to give 28 g (83% yield).

F. & G. A mixture of E (28 g, 0.88 mole), absolute alcohol (300 ml) and aminoacetaldehyde dimethyl acetal (10.5 g, 0.10 mole) was refluxed for 3 hours. The solvent was removed by distillation under reduced pressure and the residue was heated for 20 hours at 65°–73° C. in 3N HCl. The solid was filtered, washed with water and air-dried to give 26 g. This material was dissolved in hot isopropanol (ca. 250 ml) and treated with Darco. After filtration, the solvent was removed on a rotary evaporator and the residue was triturated with acetonitrile to give 13 g (45% yield) of 2-[5-(2-bromophenyl)-2-furanyl]imidazole hydrochloride tetartohydrate (G). An analytical sample of G ([m.p. 247–250° C. (dec)] was prepared by recrystallization from acetonitrile.

Anal. Calc'd for $C_{13}H_9BrN_2O \cdot HCl \cdot \frac{1}{4}H_2O$: C, 47.28; H, 3.05; N, 8.48; $H_2O$, 1.4. Found: C, 47.29; H, 3.37; N, 8.44; $H_2O$, 1.08.

EXAMPLE 40

2-[5-(2-Bromophenyl)-2-furanyl]-4-methyl-1H-imidazole Hydrochloride (Compound of Example 32)

H. To a solution of E from Example 39 (7.2 g, 0.0257 mole) in methanol (400 ml) was added anhydrous ammonium chloride (2.574 g, 0.0481 mole). After stirring the mixture 24 hours, it was refluxed $5\frac{1}{2}$ hours and then cooled to room temperature. The solution was concentrated to a reside which was stirred in water (70 ml) for $\frac{1}{2}$ hour and then filtered. Air drying the amidine gave 7.71 g (92% yield) of 5-(2-bromophenyl)-2-furamidine hydrochloride (H).

J. H (7.71 g, 0.0256 mole) was dissolved in 125 ml of dimethylformamide (DMF—J. T. Baker Chemical Co., Phillipsburg, New Jersey) and anhydrous potassium carbonate (7.49 g, 0.0542 mole) added. After 1 hour of stirring chloracetone (2.26 ml, 2.63 g, 0.0284 mole) (Aldrich Chemical Co.) was added and stirring continued overnight. Filtering an inorganic salt out and concentrating the filtrate gave an oil which was taken up in chloroform (470 ml) and washed with water (2×250 ml). The organic layer was dried over magnesium sulfate with Darco and the filtrate then concentrated to an oil (9.42 g). Purification by the Waters Prep LC/system 500A (Waters PrePAK 500 Silica cartridge 57 mm×30 cm; 70:30 ethyl acetate:hexane—Waters Associates, Inc., Milford, Massachusetts) gave a solid which was dissolved in ethyl acetate (250 ml) and methanolic HCl was added to this solution until acidic. Collecting this precipitate and drying in vacuo (over chloroform) gave 3.26 g (37% yield) of 2-[5-(2-bromophenyl)-2-furanyl]-4-methyl-1H-imidazole hydrochloride; m.p. 197°–200° C.

Anal. calc'd for $C_{14}H_{12}BrClN_2O$: C, 49.51; H, 3.56; N, 8.25. Found: C, 49.67; H, 3.62; N, 7.95.

EXAMPLE 41

2-[5-(2-Bromophenyl)-2-furanyl]-1-ethyl-1H-imidazole Hydrochloride (Compound of Example 30)

K. Dissolving G from Example 39 (1.81 g, 0.0055 mole) in 95% ethanol (75 ml) and adding water (75–100 ml) and then saturated sodium bicarbonate solution until basic gave 1.58 g (99% yield) of free base of G of Example 39 (K) after air drying.

L. K (1.58 g, 0.0054 mole) was dissolved in DMF (50 ml) and sodium hydride (0.138 g, 0.0058 mole) added at −15° C. using a methanol/ice bath. The mixture was stirred $1\frac{1}{2}$ hours and then iodoethane (0.44 ml, 0.858 g, 0.0055 mole) (Aldrich Chemical Co.) was added and stirring continued overnight.

The solution was concentrated to a residue which was dissolved in chloroform (100 ml) and washed with 1N NaOH (2×150 ml) and then water (2×150 ml). Drying the organic layer over magnesium sulfate and concentrating the filtrate gave an oil which precipitated a hydrochloride salt upon dissolving in ethyl acetate (200 ml) and adding methanolic HCl until acidic. Collecting the solid and triturating in hot ethyl acetate give 1.18 g (76% yield) of 2-[5-(2-bromophenyl)-2-furanyl]-1-ethyl-1H-imidazole hydrochloride; m.p. 233°–234° C.

Anal. calc'd for $C_{15}H_{14}BrClN_2O$: C, 50.94; H, 3.99; N, 7.92. Found: C, 50.47; H, 3.99; N, 8.18.

EXAMPLE 42

2-[5-(4-Bromophenyl)-2-furanyl]-4-methyl-1H-imidazole Hydrochloride (Compound of Example 23)

A. & B. A mixture of 500 g (2.9 moles) of 4-bromoaniline (Aldrich Chemical Co.) in 582 ml of water and 1310 ml of concentrated HCl was heated to 80° C. to form the hydrochloride, cooled to 0° C. and diazotized by the dropwise addition of 203.5 g (2.95 moles) of $NaNO_2$ in 814 ml of water over a period of 1 hour 10 minutes at 0°–5° C. The resulting solution was stirred at 0° C. for 1 hour and then treated with 279 g (2.9 moles) of furfural followed by a solution of 67 g (0.39 moles) of cupric chloride dihydrate in 291 ml of water. The cooling bath was removed and stirring was continued for 20 hours during which time the mixture self-heated at 66° C. (after 5 hours). Crystallization of the oily product was induced by stirring the mixture with 1100 ml of ether for 2 hours. The solid was isolated by filtration and then dried to give 253 g (34.8% yield) of greenish gray solid. Recrystallization from 2700 ml of ethyl acetate (30 g Darco) followed by drying at 65° C. gave 184 g (72.7% recovery, 25.3% yield) of 5-(4-bromophenyl)-2-furancarboximidamide hydrochloride (B) as a tan solid; m.p. 156.5°–158° C.

C. A solution of hydroxylamine hydrochloride (7 g, 0.1 mole) in water (20 ml) was added to a solution of B (25 g, 0.1 mole) in ethanol (150 ml) and stirred for 1 hour. The mixture was cooled overnight and the product, 5-(4-bromophenyl)-2-furaldehyde oxime (C), was collected by filtration; yield: 25 g (93%).

D. A stirred mixture of C (25 g, 0.1 mole) and benzene (400 ml) was heated to reflux and a solution of $POCl_3$ (6 ml) in benzene (30 ml) was added dropwise over 15 minutes. The mixture was refluxed for an additional $1\frac{1}{2}$ hours and filtered while hot. The filtrate was washed with 5% NaHCO₃ (600 ml) and water (600 ml), dried over MgSO₄ and Darco and filtered. The filtrate was stripped of solvent under reduced pressure, yield: 24 g (96%) of 5-(4-bromophenyl)-2-furonitrile (D).

E. Dry HCl was passed into a solution of D (24 g, 0.087 mole) in absolute methanol (100 ml) with stirring at 10–15° C. for 1½ hours. The ice bath was removed and the mixture was stirred for an additional 1 hour. The product, methyl 5-(4-bromophenyl)-2-furimidate hydrochloride (E), was collected by filtration; yield: 17 g (59%).

M. A mixture of E (17 g, 0.057 mole), NH₄OAc (80 g) and absolute alcohol (550 ml) was refluxed for 6 hours and stored overnight at room temperature. The mixture was poured onto ice, adjusted to pH 8 with NH₄OH, and concentrated to one half its volume. More water (800 ml) was added and the product was collected by filtration. The product was dissolved in isopropanol, adjusted to pH 3 with ethanol-HCl, cooled, and the product, 5-(p-bromophenyl)-2-furamidine hydrochloride (M), collected by filtration; yield: 4 g (23%); m.p. >300° C.

Anal. calc'd for $C_{11}H_9BrN_2O \cdot HCl$: C, 43.81; H, 3.34; N, 9.29. Found: C, 43.89; H, 3.44; N, 9.00.

N. M (2.98 g, 0.0099 mole) and anhydrous potassium carbonate (2.792 g, 0.0202 mole) were combined in DMF (50 ml) and the mixture cooled in an ice bath. Chloroacetone (0.8 ml, 0.0100 mole) was 048958672 added dropwise and stirring was continued for 24 hours. Heating gently for ½ hour turned the mixture orange in color. An inorganic salt was filtered off and the filtrate was concentrated to an oil which was dissolved in chloroform (125 ml) and washed with water (3×100 ml). The organic layer was dried over anhydrous magnesium sulfate and Darco added. Filtering and concentrating under reduced pressure gave an oil which upon trituration with ether gave a pale yellow solid. Dissolving in hot ethyl acetate, adding methanolic HCl until acidic and collecting the salt by filtration gave 0.97 g (29% yield) of 2-[5-(4-bromophenyl)-2-furanyl]-4-methyl-1H-imidazole hydrochloride (N); m.p. 269°–275° C. (dec.).

Anal. calc'd for $C_{14}H_{12}BrClN_2O$: C, 49.51; H, 3.56; N, 8.25. Found: C, 49.43; H, 3.52; N, 8.37.

EXAMPLES 43 AND 44

2-[5-(4-Bromophenyl)-2-furanyl]-1,4-dimethyl-1H-imidazole Hydrochloride Hydrate and
2-[5-(4-Bromophenyl)-2-furanyl]-1,5-dimethyl-1H-imidazole Hydrochloride (Compounds of Examples 33 and 34)

To a solution of N of Example 42 (3.55 g, 0.0117 mole) in DMF (100 ml) was added sodium hydride (0.945 g, 60% dispersion in mineral oil) (Aldrich Chemical Co.) at −15° C. to −20° C. pot temperature. After stirring the mixture for 2–3 hours, iodomethane (0.93 ml, 2.12 g, 0.0149 mole) (Aldrich Chemical Co.) was added and stirring continued overnight. Concentrating the reaction gave a residue which was dissolved in chloroform (125 ml) and extracted with water (3×100 ml), 1N NaOH (3×100 ml), and water (3×100 ml) again. The chloroform solution was dried and concentrated to a solid (2.71 g, 73%). This solid was chromatographed (CHCl₃/EtOAc, 50:3 as eluent) using a low pressure column of silica gel to give 0.615 g of 1,4-dimethyl isomer and 0.307 g of 1,5-dimethyl isomer.

Dissolving the 1,4 isomer in ethyl acetate and adding methanolic HCl precipitated a solid. Collecting the salt gave 0.50 g (72% yield) of 2-[5-(4-bromophenyl)-2-furanyl]-1,4-dimethyl-1H-imidazole hydrochloride hydrate; m.p. 235°–240° C.

Anal. calc'd for $C_{15}H_{13}BrN_2O \cdot HCl{\frac{1}{4}}H_2O$: C, 50.30; H, 4.08; N, 7.82. Found: C, 50.03; H, 4.05; N, 7.74.

Dissolving the 1,5 isomer in ethyl acetate and adding methanolic HCl precipitated a solid. Collecting the salt gave 0.26 g (76% yield) of 2-[5-(4-bromophenyl)-2-furanyl]-1,5-dimethyl-1H-imidazole hydrochloride; m.p. 245°–256° C.

Anal. calc'd for $C_{15}H_{13}BrN_2O \cdot HCl$: C, 50.94; H, 3.99; N, 7.92. Found: C, 50.78; H, 3.97; N, 7.76.

Another aspect of the present invention is a composition in dosage unit form comprising an effective amount of the novel 2-95-phenyl-2-furanyl)imidazoles disclosed hereinabove. The composition is preferably adapted to systemic administration to mammals.

As used herein, the term "pharmaceutical carrier" denotes a solid or liquid filler, diluent, or encapsulating substance. Some examples of the substances which can serve as pharmaceutical carriers are sugars, such as lactose, glucose, and sucrose; starches, such as corn starch and potato starch; cellulose and its derivatives, such as sodium carboxymethylcellulose, ethylcellulose, and cellulose acetate; powdered tragacanth; malt; gelatin; talc; stearic acid; magnesium stearate; calcium sulfate; vegetable oils, such as peanut oil, cottonseed oil, sesame oil, olive oil, corn oil, and oil of theobroma; polyols, such as propylene glycol, glycerin, sorbitol, mannitol, and polyethyleneglycol; agar; alginic acid; pyrogen-free water; isotonic salines; and phosphate buffer solutions; as well as other nontoxic compatible substances used in pharmaceutical formulations. Wetting agents and lubricants, such as sodium lauryl sulphate, as well as coloring agents, flavoring agents and preservatives, can also be present.

The pharmaceutical carrier employed in conjunction with the cardiotonic 2-(5-phenyl-2-furanyl)imidazoles is used at a concentration sufficient to provide a practical size-to-dosage relationship. Preferably, the pharmaceutical carrier comprises from about 0.1% to about 99% by weight of the total composition.

Preferred dosage unit forms of the compositions of the present invention include capsules, tablets, solutions, and suspensions to be administered orally and solutions and suspensions to be administered parenterally. Preferred dosage unit forms include solutions and suspensions to be administered parenterally comprising from about 10 mg to about 500 mg of a novel cardiotonic 2-(5-phenyl-2-furanyl)-imidazole and a suitable pharmaceutical carrier; more preferred is such a dosage unit form comprising from about 50 mg to about 200 mg of such compound. Other preferred dosage unit forms include capsules and tablets each comprising from about 50 mg to about 2000 mg of a novel cardiotonic 2-(5-phenyl-2-furanyl)imidazole and a suitable pharmaceutical carrier; more preferred is such a dosage unit form comprising from about 100 mg to about 500 mg of such compound.

While particular embodiments of the present invention have been described, it will be obvious to those skilled in the art that various changes and modifications to the compounds and compositions disclosed herein can be made without departing from the spirit and scope of the invention. It is intended to cover, in the appended claims, all such modifications that are within the scope of this invention.

What is claimed is:

1. A method for enhancing the contractile force of cardiac muscle of a mammal which comprises systemically administering to said mammal an effective amount of a composition comprising a compound conforming to the following chemical structure:

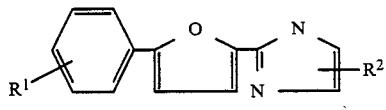

wherein $R^1$ is mono- or di- substituents selected from the group consisting of hydrogen, halo, nitro, trifluoromethyl, straight and branched chain $C_1-C_5$ alkyl, acetyl, propionyl, methoxy and ethoxy; and $R^2$ is mono- or di- substituents selected from the group consisting of hydrogen, methyl and ethyl; or a pharmaceutically acceptable salt or hydrate thereof.

2. The method of claim 1 wherein $R^2$ is hydrogen.

3. The method of claim 1 wherein $R^2$ is mono- or di- substituents selected from the group consisting of methyl and ethyl.

4. The method of claim 1 wherein $R^1$ comprises a substituent selected from the group consisting of halo and trifluoromethyl.

5. The method of claim 4 wherein $R^2$ is mono- or di- substituents selected from the group consisting of methyl and ethyl.

6. The method of claim 1 wherein $R^1$ is selected from the group consisting of hydrogen, 2-fluoro, 2-chloro, 4-chloro, 2-bromo, 4-bromo, 4iodo, 3-trifluoromethyl, 4-trifluoromethyl, 4-methyl, 4-isopropyl, 4-methoxy, 2,4-dichloro, 3,4-dichloro, 2,4-dibromo, 2-bromo-4-methyl, 2-methyl-4-bromo, 3-trifluoromethyl-4-bromo, 3-methoxy-4-bromo, and 2-nitro-4-methoxy.

7. The method of claim 6 wherein $R^2$ is hydrogen.

* * * * *